United States Patent
Dube et al.

(10) Patent No.: US 11,932,588 B2
(45) Date of Patent: Mar. 19, 2024

(54) PROCESS FOR PREPARING TRIALKYLAMMONIUM DIHYDROGEN PHOSPHATES

(71) Applicant: ENTEGRIS, INC., Billerica, MA (US)

(72) Inventors: Jonathan W. Dube, Bowmanville (CA); Christopher Brown, Toronto (CA); Keith Hao-Kiet Huynh, Toronto (CA); Hitendra Patel, Toronto (CA)

(73) Assignee: ENTEGRIS, INC., Billerica, MA (US)

( * ) Notice: Subject to any disclaimer, the term of this patent is extended or adjusted under 35 U.S.C. 154(b) by 0 days.

(21) Appl. No.: 17/984,705

(22) Filed: Nov. 10, 2022

(65) Prior Publication Data

US 2023/0159432 A1    May 25, 2023

Related U.S. Application Data

(60) Provisional application No. 63/281,110, filed on Nov. 19, 2021.

(51) Int. Cl.
*C07C 209/86* (2006.01)
*C07C 209/68* (2006.01)

(52) U.S. Cl.
CPC .......... *C07C 209/86* (2013.01); *C07C 209/68* (2013.01)

(58) Field of Classification Search
None
See application file for complete search history.

(56) References Cited

U.S. PATENT DOCUMENTS 3,838,072 A    9/1974 Smith

FOREIGN PATENT DOCUMENTS

JP    2004137163 A    5/2004
WO    2009024997 A1    2/2009

OTHER PUBLICATIONS

Singh et al., Synthesis, characterization and ion exchange properties of zirconium(IV) triethylammonium phosphate, Indian journal of chemistry, vol. 41A, pp. 2526-2529, 2002. (Year: 2002).*
Wang et al. (Green Chemistry, 2006, 8, 603) (Year: 2006).*
Ganeshpure et al., Application of triethylammonium salts as ionic liquid catalyst and medium for Fischer esterification, Arkivoc, pp. 273-278, 2007.
Singh et al., Synthesis, characterization and ion exchange properties of zirconium(IV) triethylammonium phosphate, Indian journal of chemistry, vol. 41A, pp. 2526-2529, 2002.
Attri et al., Influence of Reactive Oxygen Species on the Enzyme Stability and Activity in the Presence of Ionic Liquids, PLoS One, vol. 8, No. 9, pp. 1-11, 2013.
Li, Haoran et al., Preparation of simple ammonium ionic liquids and their application in the cracking of dialkoxypropanes, Green Chemistry, 2006, 8, 603-607.
Li, Haoran et al., Preparation of dialkoxypropanes in simple ammonium ionic liquids, Green Chem., 2006, 8, 1076-1079.
Li, Haoran et al., Novel quaternary ammonium ionic liquids and their use as dual solvent-catalysts in the hydrolytic reaction, Green Chem., 2006, 8, 96-99.

* cited by examiner

*Primary Examiner* — Sudhakar Katakam
*Assistant Examiner* — Jennifer C Sawyer

(57) ABSTRACT

The disclosure provides a process for preparing solid tri($C_1$-$C_4$ alkyl)ammonium dihydrogen phosphates such as triethylammonium dihydrogen phosphate, in high yield, and in a free-flowing particulate form. The solid product advantageously possesses less than about 1500 ppm of aprotic organic solvents, less than about 1500 ppm of $C_1$-$C_5$ alkanols, and less than about 500 ppm of water, as determined by Karl Fischer titration.

17 Claims, No Drawings

PROCESS FOR PREPARING TRIALKYLAMMONIUM DIHYDROGEN PHOSPHATES

CROSS-REFERENCE TO RELATED APPLICATIONS

This application claims the benefit under 35 USC 119 of U.S. Provisional Patent Application No. 63/281,110, filed Nov. 19, 2021, the disclosure of which is hereby incorporated herein by reference in its entirety.

TECHNICAL FIELD

The disclosure relates generally to a process for preparing solid trialkylammonium dihydrogen phosphates.

BACKGROUND

Triethylammonium dihydrogen phosphate (CAS No. 35365-94-7) is sometimes prepared as a liquid insofar as its highly hygroscopic nature tends to readily provide a generally unworkable solid. Synthetic methods which are designed to produce a solid product are problematic given the extremely hygroscopic nature of such compounds, which have a tendency to form unworkable clumps and gels upon exposure to ambient moisture.

SUMMARY

In summary, the disclosure provides a process for preparing solid tri($C_1$-$C_4$ alkyl)ammonium dihydrogen phosphates such as triethylammonium dihydrogen phosphate, in high yield, and in a free-flowing particulate form. The solid product advantageously possesses less than about 1500 ppm of aprotic solvents, less than about 1500 ppm of $C_1$-$C_5$ alkanols, and less than about 500 ppm of water (as determined by Karl Fischer titration).

DETAILED DESCRIPTION

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The term "about" generally refers to a range of numbers that is considered equivalent to the recited value (e.g., having the same function or result). In many instances, the term "about" may include numbers that are rounded to the nearest significant figure.

Numerical ranges expressed using endpoints include all numbers subsumed within that range (e.g., 1 to 5 includes 1, 1.5, 2, 2.75, 3, 3.80, 4 and 5).

In a first aspect, the disclosure provides a process for preparing solid tri($C_1$-$C_4$ alkyl) ammonium dihydrogen phosphate, the process comprising:
a. combining a $C_1$-$C_5$ alkanol with aqueous phosphoric acid to provide a solution;
b. adding a tri($C_1$-$C_4$ alkyl)amine to the solution, thereby providing a reaction mixture, while maintaining the temperature of the reaction mixture below its boiling point and while agitating the reaction mixture;
c. adding an aprotic solvent to the reaction mixture; and
d. isolating of the resulting tri($C_1$-$C_4$ alkyl)ammonium dihydrogen phosphate as a solid.

In some embodiments, the process further includes cooling the reaction mixture to about 10° C. to about 30° C. after adding the aprotic solvent.

In some embodiments, the process further comprises wherein step b. is followed by continuing agitation of the reaction mixture until the reaction mixture is visually clear.

In certain embodiments, the molar ratio of phosphoric acid to tri($C_1$-$C_4$ alkyl)amine is about 0.8 to about 2.0, about 0.8 to about 1.8, about 0.8 to about 1.6, about 0.8 to about 1.4, about 0.8 to about 1.2, about 1.0 to about 2.0, about 1.0 to about 1.8, about 1.0 to about 1.6, about 1.0 to about 1.4, 1.0 to about 1.2, about 1.2 to about 2.0, about 1.2 to about 1.8, about 1.4 to about 2.0 and all ranges and subranges therein. In one embodiment, the molar ratio of phosphoric acid to tri($C_1$-$C_4$ alkyl)amine is about 1 to about 1.05.

As used herein, the term "tri($C_1$-$C_4$ alkyl)ammonium dihydrogen phosphates" include those species where the $C_1$-$C_4$ alkyl portions are the same or are different. Examples include trimethylammonium dihydrogen phosphate, triethylammonium dihydrogen phosphate, tripropylammonium dihydrogen phosphate, and tributylammonium dihydrogen phosphate, as well as those species where each of the $C_1$-$C_4$ alkyl moieties are different, or where two are the same and a third is different.

Suitable $C_1$-$C_5$ alkanols include methanol, n-propanol, isopropanol, n-butanol, isobutanol, sec-butanol, tert-butanol, n-pentanol, isopentanol, and sec-pentanol. In one embodiment, the $C_1$-$C_5$ alkanol is isopropanol. In one embodiment, the $C_1$-$C_5$ alkanol is present in an amount sufficient to provide a visually clear solution of phosphoric acid.

As used herein, the term "aqueous phosphoric acid" includes aqueous phosphoric acid (e.g., concentrated phosphoric acid) in an amount that is effective to react with the tri($C_1$-$C_4$ alkyl)amine to produce the desired product. The term "aqueous phosphoric acid" refers to an ingredient of the composition that is mixed or combined with other ingredients of the composition to form the composition. The term "phosphoric acid solids" refers to the non-aqueous component of an aqueous phosphoric acid ingredient, or of a composition that is prepared from aqueous phosphoric acid ingredient. The amount of phosphoric acid solids contained in a composition can be an amount that is at least about 50 weight percent based on total weight of the composition, e.g., at least 70, or at least about 80 or 85 weight percent phosphoric acid solids based on total weight of the aqueous phosphoric acid composition.

To provide a desired amount of phosphoric acid solids, the composition may contain "concentrated" phosphoric acid as an ingredient that is mixed or combined with water, to produce the aqueous phosphoric acid composition. "Concentrated" phosphoric acid refers to an aqueous phosphoric acid that contains a high or maximum amount of phosphoric acid solids in the presence of a low or minimum amount of water and substantially no other ingredients (e.g., less than 0.5 or 0.1 weight percent of any non-water or non-phosphoric acid solids materials). Concentrated phosphoric acid can typically be considered to have at least about 80 or 85 weight percent phosphoric acid solids in about 15 or 20 weight percent water. Alternately, the composition may be considered to include an amount of concentrated phosphoric acid that is diluted with water, meaning for example concentrated phosphoric acid that has been diluted with an amount of water before or after being combined with other ingredients of the aqueous phosphoric acid composition, or an equivalent formed in any manner. In one embodiment, the aqueous phosphoric acid utilized in the process is concentrated phosphoric acid.

Suitable aprotic solvents include organic solvents such as ketones, esters, nitriles, carbonates, amides, ethers, and glycol ethers. Exemplary aprotic solvents include glycol ethers, including, but not limited to, ethyl acetate, N-methylpyrrolidinone (NMP), cyclohexylpyrrolidinone, N-octylpyrrolidinone, N-phenylpyrrolidinone, methyl formate, N, N'-dimethyl formamide (DMF), tetramethylene sulfone (sulfolane), acetonitrile, acetone, butyryl lactone, butylene carbonate, ethylene carbonate, propylene carbonate, dipropylene glycol, diethylene glycol monomethyl ether, triethylene glycol monomethyl ether, diethylene glycol monoethyl ether, triethylene glycol monoethyl ether, ethylene glycol monopropyl ether, ethylene glycol monobutyl ether, diethylene glycol monobutyl ether (i.e., butyl carbitol), triethylene glycol monobutyl ether, ethylene glycol monohexyl ether, diethylene glycol monohexyl ether, ethylene glycol phenyl ether, propylene glycol methyl ether, dipropylene glycol methyl ether (DPGME), tripropylene glycol methyl ether (TPGME), dipropylene glycol dimethyl ether, dipropylene glycol ethyl ether, propylene glycol n-propyl ether, dipropylene glycol n-propyl ether (DPGPE), tripropylene glycol n-propyl ether, propylene glycol n-butyl ether, dipropylene glycol n-butyl ether, tripropylene glycol n-butyl ether, propylene glycol phenyl ether, ethylene glycol monophenyl ether, diethylene glycol monophenyl ether hexaethylene glycol monophenylether, dipropylene glycol methyl ether acetate, tetraethylene glycol dimethyl ether (TEGDE), glycerine carbonate, N-formyl morpholine, triethyl phosphate, and combinations thereof. In one embodiment, the aprotic solvent is acetone.

In one embodiment, the aprotic solvent is added over a period of time which is at least about 50 to about 350 minutes per 10 kg theoretical yield of tri($C_1$-$C_4$ alkyl) ammonium dihydrogen phosphate.

The product of the reaction, i.e., the solid tri($C_1$-$C_4$ alkyl)ammonium dihydrogen phosphate can be allowed to settle, thereby forming a supernatant layer, followed by removal of the supernatant layer and washing of the tri($C_1$-$C_4$ alkyl)ammonium dihydrogen phosphate with an aprotic solvent. The product and then be dried to provide the desired product. Alternately, the product can be placed in a centrifuge to separate the solid from the supernatant liquid, thereby facilitating the isolation of the desired solid. In a further alternative, the desired product can be isolated by filtration and dried in vacuo.

Advantageously, the product of the process, i.e., the tri($C_1$-$C_4$ alkyl)ammonium dihydrogen phosphate is thus provided as a free-flowing solid, having minimal amounts of water, aprotic solvents, and $C_1$-$C_5$ alkanols present. This form is advantageous as under ordinary handling conditions, the tri($C_1$-$C_4$ alkyl)ammonium dihydrogen phosphate, in particular triethylammonium dihydrogen phosphate, is extremely hygroscopic and tends to form difficult to handle chunks and gels. As used herein, the term "free-flowing" means a powders, granules, and particulates which are capable of being easily physically transferred from one container to another due to their inherent ability to be poured; in other words, in this form, the product is generally non-agglomerated.

Accordingly, in another aspect, the disclosure provides tri($C_1$-$C_4$ alkyl)ammonium dihydrogen phosphate in a free-flowing form. In one embodiment, the tri($C_1$-$C_4$ alkyl) ammonium dihydrogen phosphate is triethylammonium dihydrogen phosphate. In certain embodiments, the products of the process have less than about 1500 ppm, less than about 1000 ppm, or less than about 500 ppm of aprotic organic solvent and/or less than about 1500 ppm, less than about 1000, or less than about 500 ppm of $C_1$-$C_5$ alkanol, and/or exhibits a Karl Fischer titration of less than about 500 ppm, or less than about 250 ppm water.

EXAMPLES

Synthesis of Triethylammonium Dihydrogen Phosphate

In a 1 L flask, 92.2 g of 85% phosphoric acid in water (0.8 mol; 1 eq.) was combined with 200 mL of isopropanol. To this mixture was added 80.9 g of triethylamine (0.8 mol; 1 eq.) while stirring. The addition was started at 20° C. and the reaction was exothermic; a white solid was observed while addition continued and when the temperature reached 50-55° C., the solid disappeared and the reaction mixture became clear, the reaction ultimately reaching 60° C. To this product mixture was added 400 mL of acetone, while slowly cooling, ultimately to −10° C. while stirring. The solid product was then filtered under dry nitrogen and washed twice with 100 mL of acetone. The resulting solid was dried by passing dry nitrogen through the solid for 1 hour, followed by continued drying in vacuo for 1 hour to provide the title compound (150 g; 93%). $^1$H NMR (400 MHz, DMSO-D6): 1.15 (t; $^3$J=7.0 Hz, 3H), 2.93 (q; $^3$J=7.0 Hz, 2H), 9-11 (br, 3H); trace solvents: acetone 2.10 (s); isopropanol: 1.04 (d), 3.77 (sept); $^{13}$C{$^1$H} (100.7 MHz, DMSO-D6): 9.3, 45.4; $^{31}$P{$^1$H} NMR (162.0 MHz, DMSO-D6): 1.05 ppm; Trace solvents ($^1$H NMR): 1060 ppm acetone, 1450 ppm isopropanol; KF titration 150 ppm.

Example 2—Synthesis of Triethylammonium Dihydrogen Phosphate in 100 L Reactor

In a 100 L reactor, 8.6 kg (5.1 L) of concentrated (85%) phosphoric acid (74.4 mol; 1 eq.) and 13.0 kg (16.6 L) of isopropanol were combined. To this mixture was added 8.0 kg (11.0 L) of triethylamine (78.9 mol; 1.06 eq.) over 3.5 hours; as this reaction is exothermic, the reaction was maintained at a temperature below 50° C. and under a blanket of dry nitrogen. After the addition of the first 1 kg of triethylamine, the reactor jacket was set to 40° C. to maintain a minimum temperature during the rest of the addition. After the triethylamine addition was complete the reactor was set to 55° C. and stirred for 1 hour. Then, the reaction mixture was treated with about 30 kg (38.2 L) of acetone, which served as an antisolvent for the resulting solid triethylammonium dihydrogen phosphate. The acetone was added slowly over 4.5 hours maintaining a minimum temperature of 45° C. The temperature of the reactor was slowly decreased to 20° C. by a ramp approach over 5 hours to precipitate the product. The resulting product was filtered and washed with additional acetone (2×10 kg), and dried in vacuo to provide the title compound as a white solid (13.2 kg; 89%). NMR data consistent with that reported on the 150 g scale. Trace solvents ($^1$H NMR): 217 ppm acetone, 933 ppm isopropanol; KF titration 70 ppm.

Example 3—Synthesis of Triethylammonium Dihydrogen Phosphate in 450 L Reactor

In a 450 L reactor, 39.0 kg (23.0 L) of concentrated (85%) phosphoric acid (334.8 mol; 1 eq.) and 59.2 kg (75.3 L) of isopropanol were combined with the reactor jacket cooled to 10° C. To this mixture was added 36.4 kg (50.1 L) of triethylamine (359.7; 1.07 eq.) over 5 hours; as this reaction is exothermic, the reaction was maintained at a temperature below 52° C. and under a blanket of dry nitrogen. After the addition of the first 1 kg of triethylamine, the reactor jacket was set to 40° C. to maintain a minimum temperature during the rest of the addition. After the triethylamine addition was complete the reactor was set to 55° C. and stirred for 1 hour. Then, the reaction mixture was treated with about 137 kg (174.7 L) of acetone, which served as an antisolvent for the resulting solid triethylammonium dihydrogen phosphate. The acetone was added slowly over 7 hours maintaining a minimum temperature of 45° C. The temperature of the reactor was slowly decreased to 20° C. by a ramp approach over 10 hours to precipitate the product. The resulting product was filtered and washed with additional acetone (2×45 kg), and dried in vacuo to provide the title compound as a white solid (61 kg; 91%). NMR data consistent with that reported on the 150 g scale. Trace solvents ($^1$H NMR): 339 ppm acetone, 902 ppm isopropanol; KF titration 250 ppm.

ASPECTS

In a first aspect, the disclosure provides a process for preparing solid tri($C_1$-$C_4$ alkyl) ammonium dihydrogen phosphate, the process comprising:
a. combining a $C_1$-$C_5$ alkanol with aqueous phosphoric acid to provide a solution;
b. adding a tri($C_1$-$C_4$ alkyl)amine to the solution, thereby providing a reaction mixture, while maintaining the temperature of the reaction mixture below its boiling point and while agitating the reaction mixture;
c. adding an aprotic solvent to the reaction mixture; and
d. isolating of the resulting tri($C_1$-$C_4$ alkyl)ammonium dihydrogen phosphate as a solid.

In a second aspect, the disclosure further provides cooling the reaction mixture to about 10° C. to about 30° C. after adding the aprotic solvent.

In a third aspect, the disclosure provides the process of the first or second aspect, wherein the reaction mixture is agitated until the reaction mixture is visually clear.

In a fourth aspect, the disclosure provides the process of any preceding aspect, wherein the molar ratio of phosphoric acid to tri($C_1$-$C_4$ alkyl)amine is about 0.8 to about 2.0.

In a fifth aspect, the disclosure provides the process of any preceding aspect, wherein the $C_1$-$C_5$ alkanol is chosen from methanol, n-propanol, isopropanol, n-butanol, isobutanol, sec-butanol, tert-butanol, n-pentanol, isopentanol, and sec-pentanol.

In a sixth aspect, the disclosure provides the process of any preceding aspect, wherein the $C_1$-$C_5$ alkanol is isopropanol.

In a seventh aspect, the disclosure provides the process of any preceding aspect, wherein the $C_1$-$C_5$ alkanol is present in an amount sufficient to provide a visually clear solution of phosphoric acid.

In an eighth aspect, the disclosure provides the process of any preceding aspect, wherein the aprotic solvent is chosen from acetone and ethyl acetate.

In a ninth aspect, the disclosure provides the process of any preceding aspect, wherein the aprotic solvent is added over a period of time which is at least about 50 to about 350 minutes per 10 kg theoretical yield of tri($C_1$-$C_4$ alkyl) ammonium dihydrogen phosphate.

In a tenth aspect, the disclosure provides the process of any preceding aspect, wherein the resulting tri($C_1$-$C_4$ alkyl) ammonium dihydrogen phosphate solid is allowed to settle, thereby forming a supernatant layer, followed by removal of the supernatant layer and washing of the tri($C_1$-$C_4$ alkyl) ammonium dihydrogen phosphate with an aprotic solvent.

In an eleventh aspect, the disclosure provides the process of any preceding claim, further comprising drying the tri ($C_1$-$C_4$ alkyl)ammonium dihydrogen phosphate.

In a twelfth aspect, the disclosure provides the process of any preceding aspect, wherein the tri($C_1$-$C_4$ alkyl)ammonium dihydrogen phosphate solid is isolated by filtration and dried.

In a thirteenth aspect, the disclosure provides the process of any preceding aspect, wherein the tri($C_1$-$C_4$ alkyl)ammonium dihydrogen phosphate is a free-flowing particulate.

In a fourteenth aspect, the disclosure provides the process of the thirteenth aspect, wherein the free-flowing particulate has less than about 1500 ppm of aprotic organic solvent and less than about 1500 ppm of $C_1$-$C_5$ alkanol.

In a fifteenth aspect, the disclosure provides the process of the thirteenth aspect, wherein the free-flowing particulate has less than about 1000 of aprotic organic solvent, and less than about 1000 ppm of $C_1$-$C_5$ alkanol.

In a sixteenth aspect, the disclosure provides the process of any one of the twelfth through fifteenth aspects, wherein the free-flowing particulate exhibits a Karl Fischer titration of less than about 500 ppm water.

In a seventeenth aspect, the disclosure provides the process of any of the twelfth through sixteenth aspect, wherein the free-flowing particulate is triethylammonium dihydrogen phosphate.

In an eighteenth aspect, the disclosure provides a free-flowing particulate form of tri($C_1$-$C_4$ alkyl) ammonium dihydrogen phosphate.

In a nineteenth aspect, the disclosure provides the free-flowing particulate form of the eighteenth aspect, wherein the tri($C_1$-$C_4$ alkyl) ammonium dihydrogen phosphate is triethylammonium dihydrogen phosphate.

In a twentieth aspect, the disclosure provides the free-flowing particulate form of the nineteenth aspect, wherein the triethylammonium dihydrogen phosphate is amorphous.

In a twenty-first aspect, the disclosure provides the free-flowing particulate form of any of the eighteenth through twentieth aspects having less than about 1500 ppm of aprotic organic solvent and less than about 1500 ppm of $C_1$-$C_5$ alkanol.

In a twenty-second aspect, the disclosure provides the free-flowing particulate form of any of the eighteenth through twentieth aspects having less than about 1000 ppm of aprotic organic solvent and less than about 1000 ppm of $C_1$-$C_5$ alkanol.

In a twenty-third aspect, the free-flowing particulate form of any of the eighteenth through twentieth aspects having less than about 500 ppm of aprotic organic solvent and less than about 500 ppm of $C_1$-$C_5$ alkanol.

In a twenty-fourth aspect, the disclosure provide the free-flowing particulate form of any one of the eighteenth through twenty-third aspects, wherein the free-flowing particulate exhibits a Karl Fischer titration of less than about 500 ppm water.

In a twenty-fifth aspect, the disclosure provides the free-flowing particulate form of any one of the eighteenth through twenty-third aspects, wherein the free-flowing particulate exhibits a Karl Fischer titration of less than about 250 ppm water.

Having thus described several illustrative embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respects, only illustrative. The disclosure's scope is, of course, defined in the language in which the appended claims are expressed.

What is claimed is:

1. A process for preparing solid tri($C_1$-$C_4$ alkyl) ammonium dihydrogen phosphate, the process comprising:
   a. combining a $C_1$-$C_5$ alkanol with aqueous phosphoric acid to provide a solution;
   b. adding a tri($C_1$-$C_4$ alkyl)amine to the solution, thereby providing a reaction mixture, while maintaining the temperature of the reaction mixture below its boiling point and while agitating the reaction mixture;
   c. adding an aprotic solvent to the reaction mixture; and
   d. isolating of the resulting tri($C_1$-$C_4$ alkyl)ammonium dihydrogen phosphate as a solid.

2. The process of claim 1, further comprising cooling the reaction mixture to about 10° C. to about 30° C. after adding the aprotic solvent.

3. The process of claim 1, wherein the reaction mixture is agitated until the reaction mixture is visually clear.

4. The process of claim 1, wherein the molar ratio of phosphoric acid to tri($C_1$-$C_4$ alkyl)amine is about 0.8 to about 2.0.

5. The process of claim 1, wherein the $C_1$-$C_5$ alkanol is chosen from methanol, n-propanol, isopropanol, n-butanol, isobutanol, sec-butanol, tert-butanol, n-pentanol, isopentanol, and sec-pentanol.

6. The process of claim 1, wherein the $C_1$-$C_5$ alkanol is isopropanol.

7. The process of claim 1, wherein the $C_1$-$C_5$ alkanol is present in an amount sufficient to provide a visually clear solution of phosphoric acid.

8. The process of claim 1, wherein the aprotic solvent is chosen from acetone and ethyl acetate.

9. The process of claim 1, wherein the aprotic solvent is added over a period of time which is at least about 50 to about 350 minutes per 10 kg theoretical yield of tri($C_1$-$C_4$ alkyl)ammonium dihydrogen phosphate.

10. The process of claim 1, wherein the resulting tri($C_1$-$C_4$ alkyl)ammonium dihydrogen phosphate solid is allowed to settle, thereby forming a supernatant layer, followed by removal of the supernatant layer and washing of the tri($C_1$-$C_4$ alkyl)ammonium dihydrogen phosphate with an aprotic solvent.

11. The process of claim 1, further comprising drying the tri($C_1$-$C_4$ alkyl)ammonium dihydrogen phosphate.

12. The process of claim 1, wherein the tri($C_1$-$C_4$ alkyl)ammonium dihydrogen phosphate solid is isolated by filtration and dried.

13. The process of claim 1, wherein the tri($C_1$-$C_4$ alkyl)ammonium dihydrogen phosphate is a free-flowing particulate.

14. The process of claim 13, wherein the free-flowing particulate has less than about 1500 ppm of aprotic organic solvent and less than about 1500 ppm of $C_1$-$C_5$ alkanol.

15. The process of claim 13, wherein the free-flowing particulate has less than about 1000 of aprotic organic solvent, and less than about 1000 ppm of $C_1$-$C_5$ alkanol.

16. The process of claim 13, wherein the free-flowing particulate exhibits a Karl Fischer titration of less than about 500 ppm water.

17. The process of claim 13, the free-flowing particulate is triethylammonium dihydrogen phosphate.

* * * * *